United States Patent
Ahlmén et al.

(10) Patent No.: US 7,077,136 B2
(45) Date of Patent: Jul. 18, 2006

(54) ANAESTHETIC DELIVERY SYSTEM

(75) Inventors: Christer Ahlmén, Sollentuna (SE); Păr Emtell, Vällingby (SE); Mario Loncar, Ekerö (SE)

(73) Assignee: Maquet Critcal Care AB, Solna (SE)

( * ) Notice: Subject to any disclaimer, the term of this patent is extended or adjusted under 35 U.S.C. 154(b) by 0 days.

(21) Appl. No.: 10/510,854

(22) PCT Filed: Feb. 26, 2003

(86) PCT No.: PCT/SE03/00318

§ 371 (c)(1),
(2), (4) Date: Oct. 12, 2004

(87) PCT Pub. No.: WO03/090826

PCT Pub. Date: Nov. 6, 2003

(65) Prior Publication Data

US 2005/0166917 A1    Aug. 4, 2005

(30) Foreign Application Priority Data

Apr. 23, 2002 (SE) ..................... 0201212

(51) Int. Cl.
*A62B 7/10* (2006.01)
*A61M 15/00* (2006.01)
(52) U.S. Cl. .................... 128/205.27; 128/203.12
(58) Field of Classification Search ........... 128/201.23, 128/203.12, 203.14, 203.18, 203.25, 205.27, 128/205.28, 205.29, 910, 912, 914; 96/108, 96/109, 110, 111
See application file for complete search history.

(56) References Cited

U.S. PATENT DOCUMENTS

| | | | | |
|---|---|---|---|---|
| 3,592,191 | A | * 7/1971 | Jackson | 128/203.28 |
| 4,015,599 | A | 4/1977 | Peterson | |
| 4,150,670 | A | 4/1979 | Jewett et al. | |
| 5,044,361 | A | * 9/1991 | Werner et al. | 128/204.16 |
| 5,471,979 | A | 12/1995 | Psaros et al. | |
| 5,487,380 | A | * 1/1996 | Grabenkort | 128/204.15 |
| 5,794,848 | A | 8/1998 | Nunn et al. | |
| 5,934,274 | A | 8/1999 | Merrick et al. | |
| 6,152,133 | A | 11/2000 | Psaros et al. | |
| 6,286,505 | B1 | 2/2001 | Psaros | |
| 6,220,242 | B1 | 4/2001 | Wallin | |
| 6,343,603 | B1 | 2/2002 | Tuck et al. | |
| 6,745,771 | B1 | * 6/2004 | Castor et al. | 128/205.27 |
| 6,863,067 | B1 | * 3/2005 | Loncar | 128/203.12 |

* cited by examiner

*Primary Examiner*—Teena Mitchell
(74) *Attorney, Agent, or Firm*—Schiff Hardin LLP

(57) ABSTRACT

An anesthetic delivery system has a delivery unit containing a carbon dioxide retaining element and a reversible action anesthetic absorber/desorber for releasably retaining therein at least a portion of a charge of anesthetic agent. An externally accessible first internal flow section in the delivery unit directs gas through the delivery unit first through the anesthetic absorber/desorber and then through the carbon dioxide retaining element, sequentially. An externally accessible second internal flow section directs gas through the delivery unit via the anesthetic absorber/desorber and bypassing the carbon dioxide retaining element.

8 Claims, 4 Drawing Sheets

ANAESTHETIC DELIVERY SYSTEM

BACKGROUND OF THE INVENTION

1. Field of the Invention

The present invention relates to an anesthetic delivery system and in particular to a system adapted to re-use anesthetic that remains unabsorbed by a patient from a previously inhaled anesthetic dose.

2. Description of the Prior Art

It is know from U.S. Pat. No. 4,015,599 to provide an anesthetic delivery system having a delivery unit that houses a carbon dioxide absorber and a reversible action anesthetic adsorption filter arranged in series and in gaseous communication with a gas flow passage that provides a flow path for gas through the unit via the carbon dioxide absorber and the anesthetic adsorption filter. A charge of a gas-forming anesthetic is also provided as part of the system, pre-loaded into the anesthetic adsorption filter.

In use, the unit of the known anesthetic delivery system is disposed in gas flow connection with a tubing circuit of a so-called "closed" inhalation anesthesia system. The unit is intended to be used in a manner such that exhaled breathing gas within the tubing circuit passes first through the carbon dioxide absorber and then through the adsorption filter to collect. This anesthetic gas is then supplied into the tubing circuit for inhalation by the patient, together with fresh breathing gas that is added after the unit to compensate for the gas that was consumed.

SUMMARY OF THE INVENTION

An object of the present invention is to provide an anesthetic delivery system adapted for use in a so-called "open" inhalation anesthesia system and which also allows the re-use of exhaled anesthetic.

This object is achieved in accordance with the present invention by an anesthetic delivery system having a delivery unit with two internal gas flow passages, an exhalation gas flow passage that conducts gas through the adsorption filter only, and an inhalation gas flow passage that conducts gas through first the adsorption filter and then through the carbon dioxide absorber. Thus any unused anesthetic in exhalation gas is retained by the filter and is returned ("reflected"), essentially free of carbon dioxide, for re-inhalation by a patient while permitting the majority of exhaled carbon dioxide to pass through the unit. In this manner the lifetime of the anesthetic charge may be extended without increasing its size and the amount of carbon dioxide absorber material may be reduced compared to the known system, thereby enabling a reduction in material costs and size of the delivery unit.

Usefully a bypass gas flow passage may be included within the unit and configured to provide a flow path for an amount, preferably a variable amount, of gas from the inhalation passage to bypass the anesthetic filter. In this manner take up of anesthetic may be controlled by controlling the gas flow through the anesthetic adsorption filter.

A variable flow restriction may be provided within either of the bypass gas flow passage and the inhalation gas flow passage to regulate the flow of gas in the inhalation line through the filter and thereby variably control the concentration of anesthetic in the gas that passes out of the delivery unit. Usefully the variable flow restriction may be adapted to automatically regulate the flow of gas dependent on a sensed concentration of anesthetic in the gas. Preferably a material, such as silicone rubber, that reacts to change its physical dimensions in response to an exposure to anesthetic, is employed in the variable flow restriction. In this way sensing of the anesthetic concentration and the dependent control of the flow restriction may be carried out within the delivery unit without the need of additional electronic sensor or control arrangements.

The above object also in achieved in accordance with the present invention by an inhalation anesthetic system having a mechanical breathing aid which may be a ventilator or respirator of a stationary system or which may be, for example, a compressible bag or bottled gas supply, connectable to the airways of a patient by a gas flow circuit having a common gas flow section in which inhalation gas from the breathing aid can flow towards the patient and in which exhalation gas from the patient can flow towards the breathing aid. A delivery unit of the anesthetic delivery system is provided in fluid communication with the flow circuit, preferably the common gas flow section, so that inhalation gas can flow through the unit to receive a dose of the anesthetic agent held by the absorption filter and so that the exhalation gas can flow through the unit to deposit unused anesthetic agent in the absorption filter together with a small amount of the carbon dioxide present in the exhalation gas.

DESCRIPTION OF THE PREFERRED EMBODIMENTS

Figure 1:
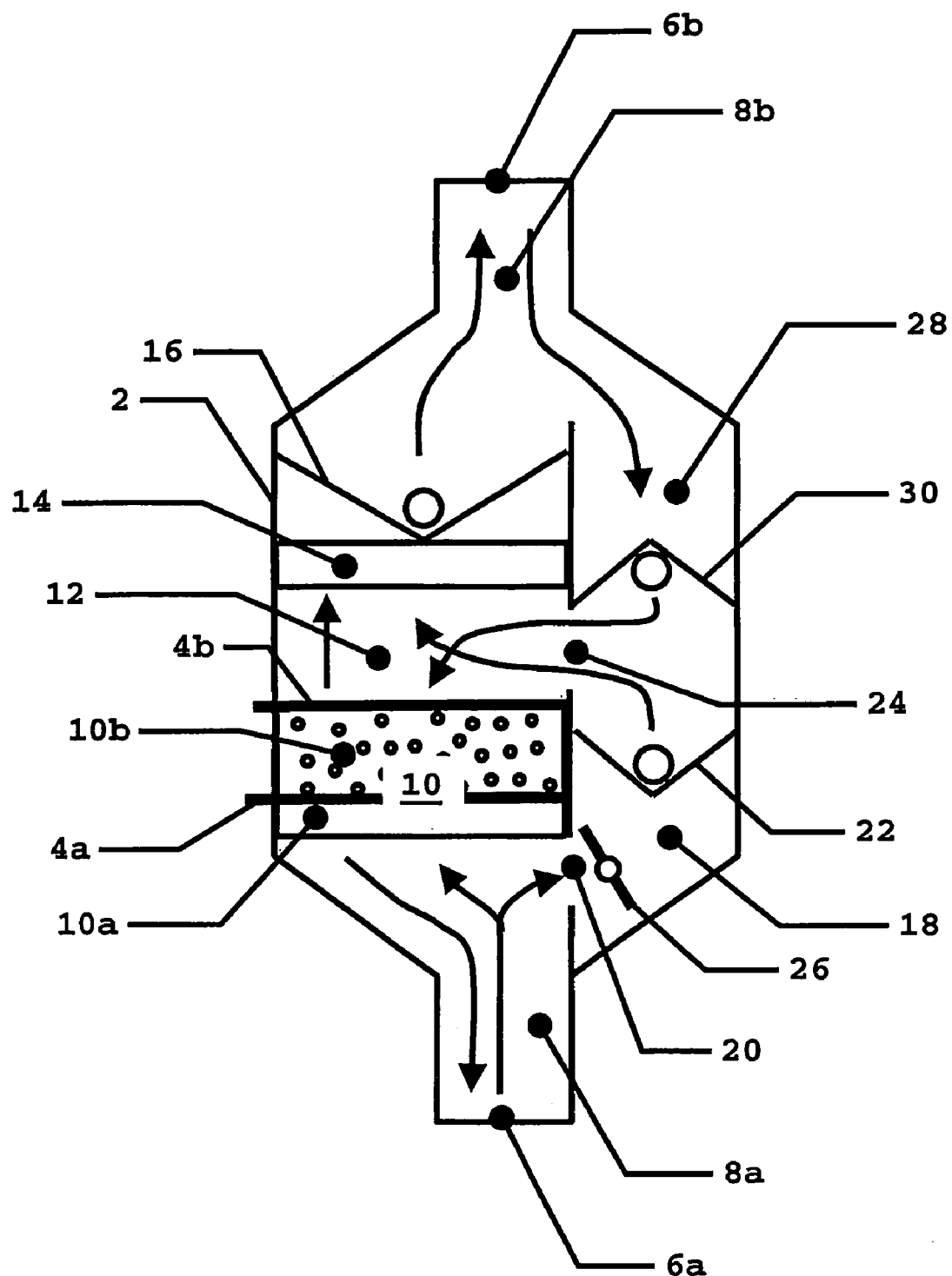
FIG. 1 shows schematically a first embodiment of an anesthetic delivery system according to the present invention.

Considering now the anesthetic delivery system of FIG. 1, a delivery unit 2 is, in the present embodiment, formed with ports 6*a*, 6*b* for providing gas communication between internal and external the unit 2. Gas flow directions through the unit 2, when in use are shown, in FIG. 1 by the arrows.

The port 6*a* provides for gas communication between external the unit 2 and a common flow passage 8*a* internal the unit 2 whilst the port 6*b* provides for gas communication between external the unit 2 and a common flow passage 8*b* internal the unit 2. These common flow passages 8*a*, 8*b* form part of both an inhalation gas flow passage (for gas flowing within the unit 2 from port 6*a*, towards the port 6*b*) and an exhalation gas flow passage (for gas flowing within the unit 2 from port 6*b*, towards the port 6*a*).

A reversible action anesthetic (adsorption/desorption) filter 10 formed of a suitable sorption material for anesthetic agent, such as zeolites of crystalline aluminum silicates which may be pellets or supported on a carrier; an activated carbon filter such as formed from carbon-impregnated material, carbon fiber cloth, or granulated or microporous carbon material; or other microporous material, is arranged in direct gas communication with the common flow passage 8*a*. In the present embodiment this anesthetic sorption filter 10 is formed into two regions. A first region 10*a* is provided initially free of the anesthetic agent and a second region 10*b* is pre-loaded with an anesthetic agent to be delivered to a patient. Optionally and as illustrated in the present embodiment, a first removable sealing membrane 4a, such as may be formed from an impermeable plastics material, is located between the first region 10a and the second region 10b to act as a barrier for the transport of the pre-loaded anesthetic agent into the second region 10b. A second removable sealing membrane 4b is located to seal the second region 10b against escape of anesthetic agent from the filter 10. The two membranes 4a, 4b are removable from the filter 10 by pulling on externally accessible tab sections and are intended to be removed immediately before use of the unit 2. In this manner the pre-loaded delivery unit 2 may be stored for extended periods without loss of anesthetic from the second region 10b of the filter 10.

The filter 10 is located within the delivery unit 2 with the anesthetic free region 10a relatively closer to the port 6a and in fluid communication with the common flow passage 8a. Pre-loading may be achieved in a number of ways, for example by passing an anesthetic containing gas, in this embodiment preferably in a direction from the port 6b to the port 6a, through the unit 2 before any removable sealing membrane 4a, 4b is in place and until a required amount of anesthetic agent has been retained by the anesthetic filter 10. This can be monitored by monitoring the anesthetic concentration in gas exiting the unit 2 through the port 6a. Pre-loading of the filter 10 may alternatively be carried out by passing an anesthetic containing gas through it before it is placed within the delivery unit 2.

A flow channel 12 is provided within the unit 2 for fluid communication between the second region 10b of the anesthetic filter 10 and a carbon dioxide absorber 14. A one-way valve 16 is disposed relative to the carbon dioxide absorber 14 to prevent gas flow into the absorber 14 from the port 6b.

A bypass gas flow passage 18 is connected through an opening 20 with the common flow passage 8a at a location between the port 6a of the unit 2 and the anesthetic filter 10.

A one-way valve 22 is provided to permit gas flow along the bypass gas flow passage 18 in a direction from the common flow passage 8a only. The bypass gas flow passage 18 is arranged to provide a flow path for gas from the port 6a to the port 6b, avoiding the anesthetic sorption filter 10 and in the present embodiment terminates at an opening 24 in the flow channel 12. A variable flow restriction 26 is provided in communication with the bypass gas flow passage 18 and is movable to vary the resistance to gas flow within the bypass gas flow passage 18.

A flow passage 28 within the delivery unit 2 communicates with the common gas flow passage 8b; with the second region 10b of the anesthetic sorption filter 10 through the opening 24 in the flow channel 12 and forms part of an exhalation gas flow passage. The flow passage 28 is here shown to be provided with a one-way valve 30 to ensure gas flow through the passage 28 in one direction only—from the port 6b towards the anesthetic filter 10, avoiding the carbon dioxide absorber 14.

Figure 2:
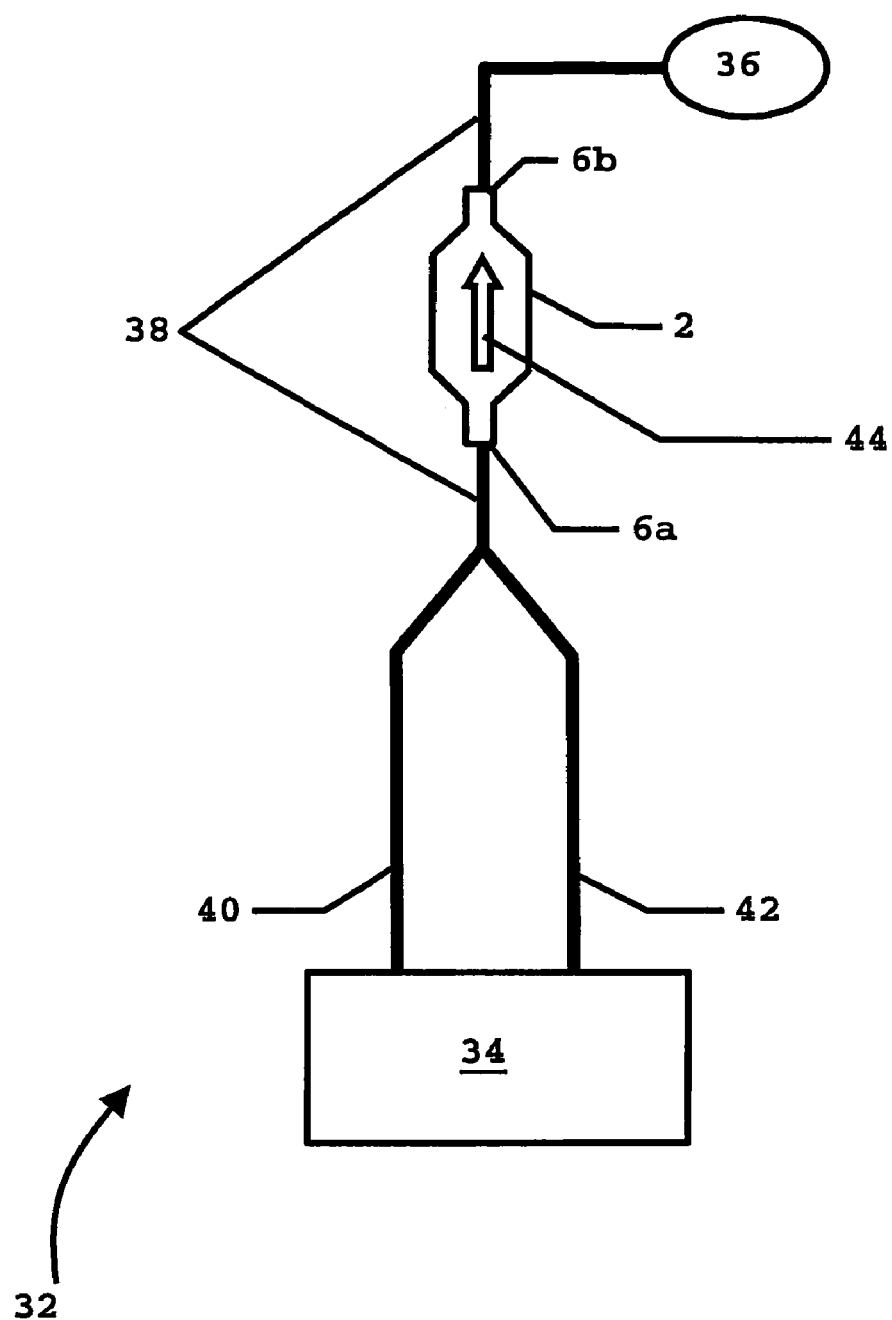
FIG. 2 is a schematic representation of an inhalation anesthetic system according to the present invention.

An exemplary "open" inhalation anesthetic system 32 is shown in FIG. 2. A mechanical breathing aid 34, such as a ventilator, is shown in use in gas communication with the airways of a patient 36. The system 32 is provided with a common gas line 38 for the delivery to and recovery from the airways of a patient 36 of anesthetic containing gases. Separate inhalation 40 and exhalation 42 gas lines are provided to connect the breathing aid 34 with the common gas line 38.

The anesthetic delivery unit 2 of FIG. 1 is shown here as being series connected to the common gas line 38 so that gas passing both to and from the patient will pass through the unit 2. The unit 2 is oriented within the common gas line 38 so that inhalation gas from the breathing aid 34 will enter the unit 2 through the port 6a and exhalation gas from the airways of the patient 36 will enter the unit 2 through the port 6b. To facilitate this orientation a visible indication, such as an arrow 44 showing the intended direction of gas flow through the unit 2 towards the patient 36, may be provided on an external surface of the unit 2.

In use the delivery unit 2 is intended to receive inhalation gas for inhalation by a patient 36 through the port 6a and into the common gas flow passage 8a. This inhalation gas may then be divided to flow partly through the anesthetic filter 10 and partly through the bypass gas flow passage 18 to avoid the filter 10. The gas flowing through the filter 10 picks up anesthetic agent together with carbon dioxide that may be present within the filter 10 and flows towards the carbon dioxide absorber 14. It will be appreciated that by moving the flow restriction 26 to alter the resistance to flow it presents then the amount of inhalation gas flowing through the absorption filter 10 can be varied and the concentration of anesthetic in the inhalation gas that exits the unit 2 through the port 6b controlled.

In the present example this anesthetic containing inhalation gas is recombined with the inhalation gas from the bypass gas flow passage 18 in the flow channel 12 before it passes through the carbon dioxide absorber 14. Carbon dioxide that was picked up by the inhalation gas as it passed through the anesthetic filter 10 will be captured by the carbon dioxide absorber 14. The essentially carbon dioxide free inhalation gas then flows through the one-way valve 16, along the common flow passage 8b and out of the delivery unit 2 through the port 6b carrying with it a dose of anesthetic for inhalation by the patient 36.

Exhalation gas from the patient 36 will typically contain carbon dioxide and an amount of unused anesthetic. In use the delivery unit 2 is intended to receive this exhalation gas through the port 6b and in to the common flow passage 8b. The combination of one-way valves 16, 22, 30 ensures that exhalation gas flows only through the exhalation flow passage 28, via the gas flow channel 12, and into the anesthetic filter 10, avoiding the carbon dioxide absorber 14. As the exhalation gas passes through the filter 10 any unused anesthetic in the gas will be retained together with a small amount of the carbon dioxide that will also be present in the exhalation gas. The substantially anesthetic free exhalation gas then flows into the common flow passage 8a and out of the unit 2 through the port 6a. In this manner the effectiveness of the delivery unit 2 in delivering anesthetic doses is prolonged since the anesthetic charge that was initially loaded into the sorption filter 10 is partially restored with unused anesthetic present in the exhalation gas that the delivery unit 2 "reflects" back to the patient's airways 36.

Figure 3:
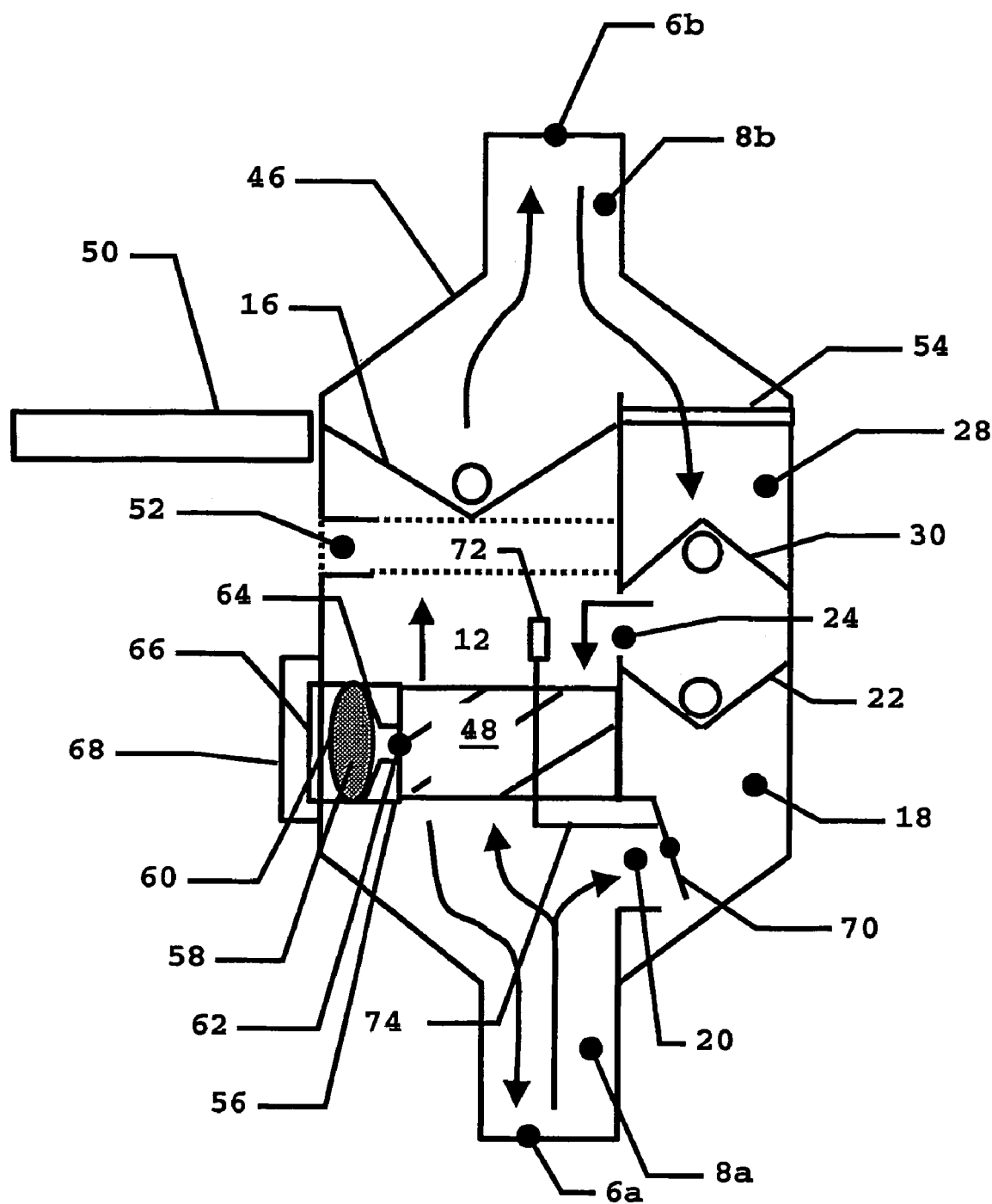
FIG. 3 shows schematically a second embodiment of an anesthetic delivery system according to the present invention.

A second embodiment of an anesthetic delivery system is shown in FIG. 3. A delivery unit 46 is configured with gas flow paths substantially similar to those illustrated in FIG. 1 and are again shown by arrows in the present figure. For ease of understanding items of the unit 46 of FIG. 3 that are substantially similar to items of the unit 2 of FIG. 1 are identified with corresponding reference numerals.

As described with respect to FIG. 1, a port 6a is provided in the unit 46 and delimits one end of a common flow passage 8a. An anesthetic filter 48 is located with a first side in gas communication with the common flow passage 8a and with a second, opposing, side for gas communication with a removable carbon dioxide filter 50 by means of a flow channel 12. The carbon dioxide filter 50, when inserted into the unit 46 (broken line construction of FIG. 2) through the co-operating access slot 52, is also located in gas communication with a second common flow passage 8*b* that is delimited at one end by a port 6*b* in the unit 46. A one-way valve 16 is disposed to prevent gas flow from the common flow passage 8*b* into the carbon dioxide filter 50.

The common flow passage 8*b* also provides for gas communication between the port 6*b* and a flow passage 28 that is arranged to communicate with the anesthetic filter 48 via an opening 24 in the common flow passage 12. A one-way valve 30 ensures that gas can only flow in the flow passage 28 in a direction from the port 6*b*.

Different from the embodiment of FIG. 1, a bacteria filter 54 is located, optionally removably located, in the flow passage 28 to prevent contamination of the anesthetic filter 48 by bacteria that may be present in exhalation gas flowing into the unit 46 through the port 6*b*.

Also different from the embodiment of FIG. 1, the delivery unit 46 of FIG. 3 contains a housing 56 in which is held a charge 58 of anesthetic agent within a frangible container 60. The housing 56 is provided with an opening 62 through which the charge 58 of anesthetic agent may flow to load the anesthetic filter 48 prior to use. The housing 56 is here also provided with internal walls 64, shaped to funnel the flow of anesthetic agent towards the opening 62. The housing 56 is further provided with an inwardly deformable wall section 66 that is accessible from external the delivery unit 46. In use, an external force may be applied to this wall section 66 to cause its deformation and a consequent transmission of the force to the frangible container 60. This results in the container 60 breaking to release the charge 58. A removable rigid cover 68 is preferably provided to overlay the deformable wall section 66 to prevent accidental breakage of the container 60. The housing 56 and the anesthetic filter 48 may be formed as a single unit, so as to be removable, within the delivery unit 46.

A bypass gas flow passage 18 is connected for fluid communication with the common flow passage 8*a* by an opening 20 and with the carbon dioxide filter 50 through the opening 24 in the flow passage 12. Similar to the embodiment of FIG. 1, a one-way valve 22 is provided to ensure that gas is able to flow through the bypass gas flow passage 18 only in the direction from the common flow passage 8*a*, towards the carbon dioxide filter 50. A vane 70 is provided within the passage 18 and is rotatable to present a variable resistance to gas flow from the common flow passage 8*a* and thereby control the amount of gas bypassing the anesthetic filter 48. The vane 70 is coupled to an anesthetic concentration sensor 72 via a linkage 74. The rotational position of the vane 70 is automatically variable to change the flow resistance it presents dependent on the concentration of anesthetic that is sensed by the sensor 72. In the present exemplary embodiment the concentration sensor 72 is formed of a silicone rubber block, a material that varies its physical dimensions in response to exposure to anesthetic, configured such that, in co-operation with the linkage 74, it will exert a force on the vane 70 tending to cause the vane 70 to rotate and present a reducing resistance with increasing anesthetic concentration at the sensor 72.

Figure 4:
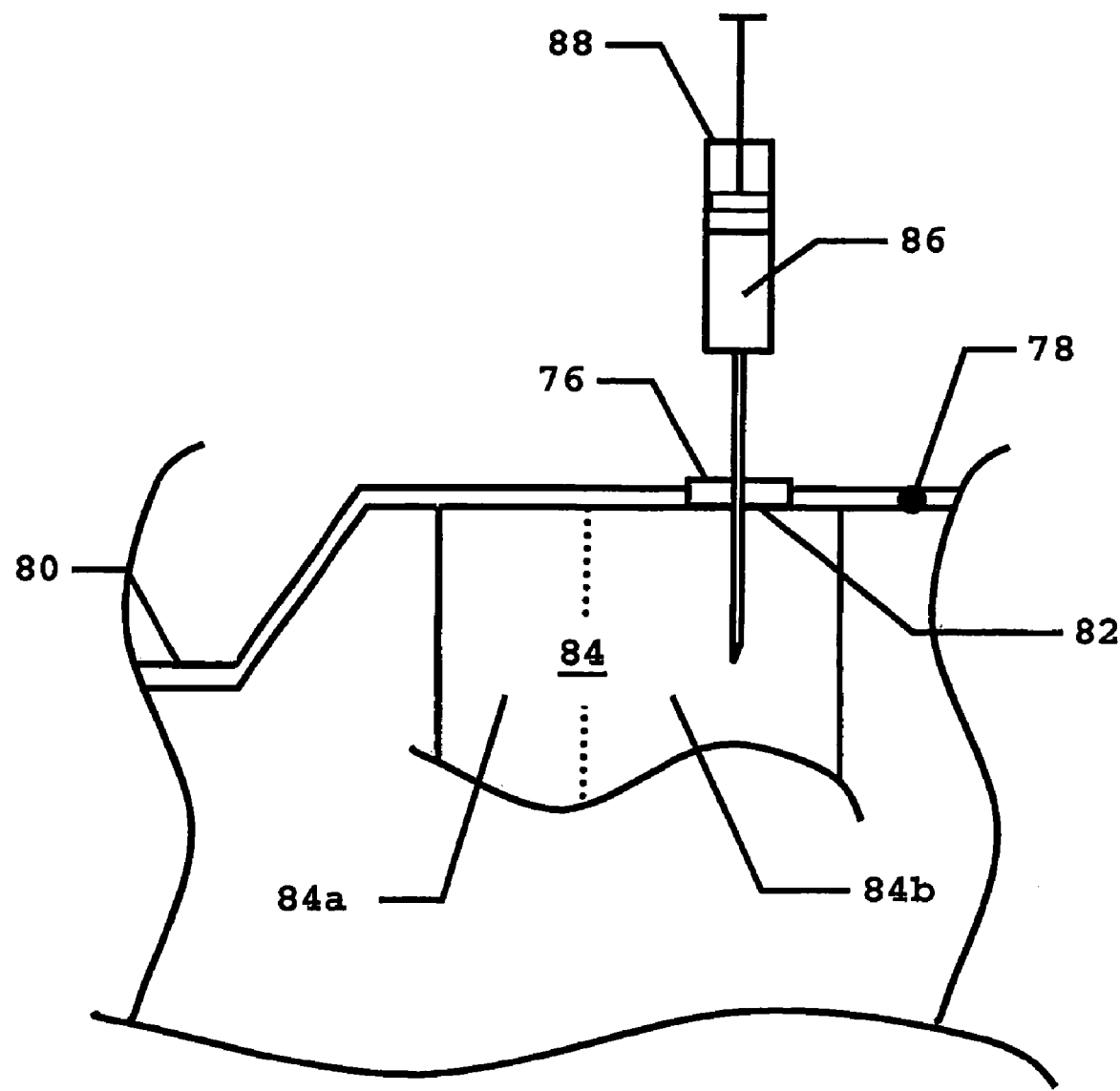
FIG. 4 shows part of a third embodiment of an anesthetic delivery system according to the present invention.

A part of third embodiment of an anesthetic delivery system according to the present invention is shown in FIG. 4 and shows an anesthetic absorption filter arrangement that may be employed as an alternative to those of FIG. 1 and FIG. 2. In this third embodiment a membrane 76 replaces part of an external wall 78 of an anesthetic delivery unit 80. The membrane 76 is of a type well known in the art of, for example implantable insulin pumps or of drug administration in ventilators, and is formed of a material that re-seals when a puncturing syringe needle is withdrawn. The membrane 76 of the present embodiment partially overlays and is presented here as being in intimate contact with an outer surface 82 of an anesthetic sorption filter 84. A charge 86 of anesthetic agent is provided in a syringe 88 for injection through the membrane 76 and into an anesthetic receiving portion 84*b* of the filter 84 to load at least part of the filter 84 with anesthetic agent for delivery to a patient. In this manner a region 84*a* of the anesthetic filter 84, which corresponds to that region 10*a* of the filter 10 of the embodiment shown in FIG. 1, may be provided that is initially substantially anesthetic free.

It will be appreciated that by using the combination of re-sealable membrane 76 and syringe 88 the sorption filter 84 may be optionally re-loaded during use. Moreover, this combination enables the filter 84 to be loaded immediately before use, which facilitates the storage of the anesthetic delivery system. Additionally the filter 84 may be loaded with an anesthetic agent of choice so that only a single construction type of delivery unit 80 needs to be manufactured.

Although modifications and changes may be suggested by those skilled in the art, it is the invention of the inventors to embody within the patent warranted heron all changes and modifications as reasonably and properly come within the scope of their contribution to the art.

We claim as our invention:

1. An anesthetic delivery system comprising:
    a delivery unit containing an anesthetic absorber/desorber and a carbon dioxide retaining element;
    an externally accessible first internal flow section in said delivery unit directing gas sequentially first through said anesthetic absorber/desorber and subsequently through said carbon dioxide retaining element;
    an externally accessible second internal flow section in said delivery unit directing gas through said delivery unit through said anesthetic absorber/desorber and bypassing said carbon dioxide retaining element; and
    a third internal flow section in said delivery unit in gaseous communication with said first internal flow section and configured to provide a flowpath for only a portion of gas from said first internal flow section to said carbon dioxide retaining element and said portion bypassing said anesthetic absorber/desorber.

2. An anesthetic delivery system as claimed in claim 1 comprising a source for a charge of anesthetic agent, in gaseous communication with said anesthetic absorber/desorber, for releasable retention by said anesthetic absorber/desorber.

3. An anesthetic delivery system as claimed in claim 1 comprising a flow divider in said delivery unit operable to vary a relative proportion of gas flow between said first internal flow section and said third internal flow section.

4. An anesthetic delivery system as claimed in claim 3 wherein said flow divider comprises a variable flow restriction presenting a variable resistance to gas flow.

5. An anesthetic delivery system as claimed in claim 4 comprising an anesthetic concentration sensor disposed in said delivery unit at a location to sense a concentration of anesthetic in gas in said first internal flow section downstream of said anesthetic absorber/desorber, said anesthetic concentration sensor being operably connected to said variable flow restriction for automatically changing said relative proportion dependent on said concentration of anesthetic.

6. An anesthetic delivery system as claimed in claim 5 wherein said anesthetic concentration sensor comprises a material having physical dimensions that change dependent on a level of exposure to said anesthetic, and comprising a mechanical linkage operably connecting said material to said variable flow restriction and moving said flow restriction dependent on said change in said physical dimensions to vary said relative proportion.

7. An anesthetic delivery system as claimed in claim 1 wherein at least one of said anesthetic absorber/desorber and said carbon dioxide retaining element is removably mounted in said delivery unit.

8. An anesthetic inhalation system comprising:
a mechanical breathing assist device providing a supply of an inhalation gas;
a gas flow circuit connected to said mechanical breathing assist device and adapted for connection to airways of a patient to transport said inhalation gas toward the patient and to transport exhalation gas, originating from the patient, away from the patient; and
an anesthetic source for dosing said inhalation gas with an anesthetic agent, said anesthetic supply comprising a delivery unit containing an anesthetic absorber/desorber and a carbon dioxide retaining element, an externally accessible first internal flow section in said delivery unit directing gas sequentially first through said anesthetic absorber/desorber and subsequently through said carbon dioxide retaining element, and an externally accessible second internal flow section in said delivery unit directing gas through said delivery unit through said anesthetic absorber/desorber and bypassing said carbon dioxide retaining element, said delivery unit being in gaseous communication with said gas flow circuit said first internal flow section forming a flowpath for said inhalation gas and said second internal flow section forming a flowpath for said exhalation gas, and comprising a third internal flow section in said delivery unit in gaseous communication with said first internal flow section and configured to provide a flowpath for only a portion of gas from said first internal flow section to said carbon dioxide retaining element and said portion bypassing said anesthetic absorber/desorber.

* * * * *